United States Patent [19]

Ho

[11] Patent Number: 5,106,746
[45] Date of Patent: Apr. 21, 1992

[54] PROCESS FOR THE IN VITRO IMMUNIZATION OF HUMAN SPLENOCYTES AGAINST TUMOR ASSOCIATED ANTIGENS

[75] Inventor: May-Kin Ho, Carlisle, Mass.

[73] Assignee: E. I. Du Pont de Nemours and Company, Wilmington, Del.

[21] Appl. No.: 736,660

[22] Filed: May 22, 1985

[51] Int. Cl.$^5$ .................. C12N 5/02; A61K 39/00
[52] U.S. Cl. .................. 435/240.25; 435/240.31; 435/240.21; 424/88
[58] Field of Search .............. 435/240.25, 240.21, 435/240.3, 240.31; 424/88, 89, 92

[56] References Cited

U.S. PATENT DOCUMENTS 4,668,629 5/1987 Kaplan .................. 435/172.2

OTHER PUBLICATIONS

Dosch, H. and Gelfand, E. W., Journal of Immunology, vol. 118, No. 1, pp. 302-308, 1977.
Mishell & Dutton, "Immunization of Dissociated Spleen Cell Cultures from Normal Mice", J. Exp. Med. 126:423 (1967).
Borrebaeck et al., Chem. Abs. 44110q, vol. 102, No. 5, p. 425, Feb. 4, 1985.
Borrebaeck, Acta Chemica Scandinavica, pp. 647-648, vol. B37, No. 7 (1983).
Ho & Durda, J. Cell. Bio., Supp. No. 9, Part A, p. 41, No. 0090 (1985).

*Primary Examiner*—Christine Nucker
*Assistant Examiner*—T. Cunningham

[57] ABSTRACT

A process for the in vitro immunization of an immunocompetent splenocyte against an immunogen comprising (a) obtaining a first human splenocyte population, (b) fractionating the first population so that the first fraction is enriched with T-cells and a second fraction is enriched with B-cells, (c) mixing together the cells from the first and second fractions to form a second population having a T-helper cell to B-cell ratio of at least 0.4, and the percentage of T-suppressor cells is essentially unchanged from the first population, and (d) culturing the second population in a medium containing human serum, an immunogen and a lymphokine or lymphokines which induce proliferation and differentiation of T and B cells.

9 Claims, No Drawings

PROCESS FOR THE IN VITRO IMMUNIZATION OF HUMAN SPLENOCYTES AGAINST TUMOR ASSOCIATED ANTIGENS

TECHNICAL FIELD

The present invention relates broadly to a process for the in vitro immunization of human splenocytes against tumor associated antigens, and more specifically, against bombesin.

BACKGROUND OF THE INVENTION

Techniques for the production of hybridomas and monoclonal antibodies are well known. All such techniques require the immunization of a lymphocyte against a preselected antigen. In many cases, especially those involving lymphocytes of non human origin, the immunization can be carried out by classical injection of the antigen into an immuno-competent host animal, followed eventually by sacrificing the animal and removing the spleen which is a fertile source of immune lymphocytes.

With increasing interest in human monoclonal antibodies, it has become necessary to devise ways of immunizing human lymphocytes in-vitro.

Hoffmann discloses a process for producing human B-lymphocytes comprising culturing human B-lymphocytes in a tissue culture medium in the presence of an antigen, helper signal producing agents comprising monocytes or monocyte conditioned medium containing Interleukin 1, helper T-lymphocytes or helper T-lymphocyte replacing factor, and homologous human serum, followed by recovering the antibody producing cells from the medium. [U.S. Pat. No. 4,444,887 issued Apr. 24, 1984 from an application filed Mar. 12, 1981.]

Cavagnaro and Osband (Biotechniques, 1, pp. 30–36 (1983)) disclose a method for the in vitro primary immunization of human peripheral blood mononuclear cells. The method requires three steps: (1) use of autologous serum (autologous with cultures; (2) depletion of suppressor lymphocytes bearing H2 histamine receptors from human peripheral blood monocyte source; and (3) use of non-specific lymphocyte activator in the immunizing cultures.

Erisman et al. describe the presence of bombesin in a human lung small-cell carcinoma grown in nude mice. Bombesin is a tetradecapeptide initially isolated from frog skin. [P.N.A.S. (USA) 79, pp. 2379–2383, (1982).]

Moody et al. disclose the bombesin levels in small cell lung, but not other types of human cancer, are routinely elevated. [Peptides, Vol. 4 pp. 683–686 (1983).]

SUMMARY OF THE INVENTION

The instant invention is a process (and product produced thereby) for the in vitro immunization of an immuno-competent human splenocyte against a clinically relevant antigen. More specifically, the process of the instant invention comprises (a) obtaining a human splenocyte population (first population), (b) fractioning the first population so that a first fraction is enriched with T-cells and a second fraction is enriched with B-cells (c) mixing together the cells from the first and second fractions to form a second population such that the second population has a T-helper cell to B-cell ratio of at least 0.4, and the percentage of T-suppressor cells is substantially unchanged from the first population, and (d) culturing the second population in a medium containing human serum, an immunogen, and a lymphokine(s) capable of inducing proliferation and differentiation of T and B cells.

DETAILED DESCRIPTION

The human splenocytes utilized in the practice of the instant invention are prepared by conventional techniques, one such technique being described in the example below. The splenocyte population so obtained is then fractionated so that a first fraction is enriched with T-cells, and a second fraction is enriched with B-cells. By "enriched" it is meant that the concentration of specific cell type is higher in the fractionated population than in the original population, preferably at least 20% higher. Other components of the splenocyte population (e.g. macrophages, granulocytes, platelets) can be contained in either the T-cell fraction or the B-cell fraction. Methods to affect the fractionation of the splenocyte population will be evident to those skilled in the art, examples being rosetting with sheep red blood cells; rosetting with red blood cells coated with anti-T or anti-B cell antibodies; panning or separation of cells on solid matrix coated with unmodified antibodies or antibodies conjugated with labels (e.g. biotin); separation of cells labeled with antibodies conjugated with fluorochromes by a fluorescence-activated cell sorter; complement-mediated lysis of cells coated with appropriate antibodies; gradient separation (e.g. 1-g sedimentation); electrophoresis; and the preferred method for purposes of the instant invention-passing the splenocyte population over a nylon wool separation column having a high surface area to volume ratio (explained in more detail in the Example below).

After fractionation of the splenocyte population, the T-cell fraction (first fraction) and the B-cell fraction (second fraction) are recombined in a manner to form a second population having a T-helper cell to B-cell ratio of at least 0.4 while maintaining the percentage of T-suppressor cells about the same as that of the original splenocyte population. By utilizing the nylon wool fractionation procedure described in the Example below, such a T-helper cell/B-cell ratio, and T-suppressor cell percentage, is obtained. If fractionation is to be carried out by one of the other methods listed above, the ratio of T-helper cells to B-cells, and the T-suppressor cell percentage, are controlled by such methods as will be apparent to those skilled in the art utilizing antibodies against helper T-cells as appropriate in those methods.

Following the fractionation and recombination steps, the second population is cultured (in appropriate tissue culture media such as RPMI-1640, Dulbecco's Modified Eagles' Media, or Iscove's Modified Dulbecco's Media) in the presence of human serum (allogeneic is preferred, although autologous may be utilized), a lymphokine(s) capable of inducing proliferation and differentiation of T and B cells, optionally a monocyte activator, and a clinically relevant immunogen.

The lymphokines useful in the practice of the subject invention will be apparent to those skilled in the art and include IL-1 and IL-2, B-cell growth factor, B-cell differentiation factor, interferon, colony-stimulating factor, thymic hormones, maturation factor and epidermal growth factor. Monocyte activators useful in the practice of the subject invention include phorbol esters, muramyl dipeptide, complement components, microbial constituents (e.g. endotoxin) interferon and interferon inducers (e.g. polyanions and viruses), mitogens, Sepharose beads and protozoa.

The selection of an immunogen against which antibodies are to be raised will, of course, depend upon clinical interest. Some clinically significant immunogens include bacterial antigens, viral antigens, toxins, blood group antigens, antigens on lymphoid cells, myosin, and tumor antigens such as cell-associated antigens and tumor cell secreted products (e.g., bombesin, CEA, AFP, HCG, calcitonin, ACTH, AVP and neurotensin). As is well known in the art, smaller antigens (mol. wt. of less than about 5000) may need to be coupled to a carrier in order to stimulate an effective immune response against the immunogen. Preferably, this carrier is an entity against which the human lymphocytes have been previously immunized, e.g. tetanus toxoid. Examples of useful carriers are keyhole-limpet hemocyanin, thyroglobulin, albumins, muramylxdipeptide, red blood cells, a solid matrix such as Sepharose beads, alkaline phosphatase, globulins, synthetic copolymers, fibrinogen and the like. Some smaller antigens may also be polymerized to increase immunogenicity. Linking agents useful in the coupling of smaller antigens to carriers include carbodiimides; glutaraldehyde; N-N-carbonyldiimidazole; 1-hydroxybenzotriazole monohydrate; N-hydroxy succinimide; N-trifluoroacetylimidazole; cyanogen bromide; and bis-diazotized benzidine. The concentration of the antigen necessary for purposes of the instant invention will depend upon the size of the antigen, and will generally be in the range of 0.1 to 100,000 ng/ml, preferably 1–10,000 ng/ml.

After culturing the splenocytes, cells are fused with an appropriate fusion partner cell line (e.g. NS-1, SHM D33, SBC H20, P3Ag8-653, SP2/0, HMy-2, WI-L2 729HF2, GM4672, and UC729-6) and the hybridoma supernatant screened for antibody production. Alternatively, cells are immortalized by transformation techniques using EBV, oncogenic DNA, etc.

Antibodies produced in accordance with the immunization protocol of the instant invention are useful in any of the well known diagnostic or therapeutic techniques currently utilizing monoclonal antibodies. The antibodies can be labeled with enzymes to be used in various enzyme linked immunoassays, with radiolabels to be used in RIAs or in in-vivo diagnosis or therapeutics, and can be used unlabeled in various competitive binding assays and therapeutic applications.

The instant invention is described in more detail in the following Example, such Example is by no means intended to limit the scope of the invention.

EXAMPLE

1. Materials and Methods

Purification of Tetanus Toxoid

Tetanus toxoid concentrate was purchased from Massachusetts State Public Health Laboratories and purified by fast protein liquid chromatography (FPLC). Typically, 5 ml of concentrate (containing 10 mg specific proteins) were applied to a 0.5×5 cm Mono Q resin column (Pharmacia, Piscataway, N.J.) which was previously equilibrated with 50 mM Bis/Tris, pH8.0. Elution was performed using a stepwise gradient with 50 mM Bis/Tris, 1M NaCl, pH8.0 as limit buffer. Greater than 95% of the tetanus toxid was recovered at 40% of the limit buffer and dialysed against 0.15M NaCl. The purity of tetanus toxoid was monitored by SDS-PAGE and reactivity with human antibodies against tetanus toxoid (Hepertet, Cutter Biological, Berkeley, CA).

Conjugation of [Lys$^3$]-Bombesin to Protein Carriers

[Lys$^3$]-bombesin (M.W. 1592), (Bachem, Burlingame, CA) was conjugated to FPLC-purified tetanus toxoid (M.W. 180,000) via 1 ethyl 3-(3-dimethyl-aminopropyl) carodiimide hydrochloride (ECDI) (Calbiochem, San Diego, CA) according to a modified procedure of Goodfriend et. al. (cite). The molar ratio of bombesin:carrier: ECDI was generally 30–60:1:6900. Briefly, [Lys$^3$]-bombesin at 2 mg/ml was added dropwise to tetanus toxoid in 0.15M NaCl followed by the dropwise addition of 200 ul of ECDI with swirling. After incubating for 15–30 minutes at room temperature, the mixture was applied to a G75 column to remove the unconjugated bombesin. Fractions containing bombesin-protein conjugates were pooled and stored at −20° C. Efficiency of conjugation was monitored by immunoreactivity with rabbit anti-bombesin (gift of Dr. L. H. Lazarus, National Institute of Environmental Health Sciences) in ELISA and by amino acid analysis.

Lymphocyte Culture Supernatants (LCS)

LCS were kindly provided by Dr. James Woody (Naval Research Center, Bethesda, MD). Briefly, they were prepared as follows. Peripheral blood lymphocytes from screened donors were cultured at 1×10$^6$/ml in RPMI-1640 medium supplemented with 0.1% purified PHA-P (Difco Laboratories, Detroit, MI) and 5% human AB serum; for 48 hours. The culture supernatants were harvested, filtered through 0.22 μm filters, and assays for interleukin-2 (IL-2) activity on an IL-2 dependent human T-cell clone. Lots with >0.8 U/ml of IL-2 were pooled and stored at 4° C. before use. Human BCGF activity was also detected in these supernatants by using a *Staphylococcus aureus* costimulator assay.

Immunofluorescent Staining

Two million human lymphocytes were incubated with 1 μg of mouse monoclonal antibody 64.1 (anti-B cells), 2H7 (anti-T cells), 66.1 (anti-helper/inducer T cells), or 51.1 (anti-cytotoxic/suppressor T cells) (DuPont-NEN Products, Boston, MA) in 100 μl of Hanks Balanced Salt Solution (GIBCO, Grand Island, N.Y.) supplemented with 2% FCS and 0.1% sodium azide for 30 minutes at 4° C. The cells were then washed three times and 100 μl of FITC-conjugated sheep F(ab')$_2$ anti-mouse Ig (DuPont-NEN) diluted 1:100 were added. After another incubation of 30 minutes at 4° C., the cells were washed three times, resuspended in phosphate-buffered saline (PBS) with 1% formalin and analysed on an EPICS V flow cytometer (Coulter, Hialeah, FL).

Enzyme-linked Immunoassays (ELISA)

Ninety-six well Immulon II plates (Dynatech, Alexandria, VA) were coated with 400 ng per well of bombesin conjugated to protein carriers of free protein carriers diluted in carbonate buffer, pH 9.6 for 18 hr. at 4° C. The plates were washed with PBS, pH 7.2, three times and blocked with PBS-1% bovine serum albumin (BSA) for 1 hour at 37° C. Subsequently, the plates were washed three times with PBS and 50 μl of hybrid supernatant fluids were added per well. After incubating for 1 hours at 37° C., the plates were again washed three times with PBS and 50 μl of horseradish peroxidase (HRP) conjugated goat anti-human Ig (Cooper Biomedical, Malvern, PA), were added per well. The plates were then incubated at 37° C. for 1 hour, washed three times with PBS, and the enzyme detected by the addition of 100 μl of o-phenylene diamine and 0.15% hydrogen peroxide. All antibodies were diluted in PBS with 0.05% Tween 20. In some experiments, HRP goat anti-human Ig was substituted by goat anti-human IgM or goat anti-human IgG (Cooper Biomedical) for isotype determination of the specific antibodies.

Competitive Inhibition Studies

Antibodies to be used in competitive inhibition studies were first titrated on plates coated with bombesin-tetanus toxoid conjugates (BTT) to determine the concentration of antibody giving half-maximal binding. This half-maximal concentration of antibody was preincubated with various concentrations of soluble inhibitors at 37° C. for 3 hours. The inhibitors included bombesin conjugated to tetanus toxoid or thyroglobulin via ECD1, tetanus toxoid, thyroglobulin, bombesin coupled to thyroglobulin by glutaraldehyde, and free [Lys$^3$]-bombesin. After preincubation, the antibodies were added to plates coated with BTT and incubated for 15 minutes at 37° C. The plates were then processed as described for routine ELISA.

In vitro Immunization

Single cell suspensions of splenocytes were prepared by teasing splenic tissues in RPMI-1640 medium (M.A. Bioproducts, Bethesda, MD.). The red cells were removed by centrifugation on a gradient of lymphocyte-separation medium (Litton Bionetics, Rockville, MD) at 1400×g for 20 minutes. Cells recovered from the interfaces were washed three times in RPMI-1640 and resuspended at $10^7$ cells/ml in ice-cold RPMI-1640 medium supplemented with 40% FCS and 10% dimethylsulfoxide. Subsequently, the cells were frozen in a controlled rate-freezer (CryoMed, St. Clemens, MI).

For sensitization, cells were thawed quickly at 37° C. and washed two times with RPMI-1640 medium. Spleen cells ($1.5-2\times10^7$) were loaded onto columns made of 0.9 g nylon wool in a 20 ml syringe barrel. The nonadherent cells were collected by elution whereas the adherent cells were harvested by alternatively washing and squeezing the nylon wool with a syringe plunger. The separated cells were washed two times in RPMI-1640 medium. One million cells of each population were added to each 16 mm culture well with antigen, 10% human AB serum (Biobee, Boston, MA), 7.5 μg/ml E coli lipopolysaccharide (Difco, Detroit, MI), and 20% pooled PHA activated lymphocyte culture supernatants (LCS). The cells in a final volume of 2 ml were cultured at 37° C. in 10% $CO_2$ for 4-6 days. The antigen was soluble [Lys$^3$]-bombesin coupled to tetanus toxoid. Typically, 3 or more concentrations of antigens were used in each experiment and 8-10 wells were set up for each concentration.

At the end of the sensitization period, the cells from identical wells were pooled and washed two times with RPMI-1640 medium. They were then fused with equal numbers of NS-1 cells using 50% polyethylene glycol (PEG, M.W. 1000) or 45% PEG (M.W. 4000) utilizing conventional protocol. The fused cells were plated at $10^5$ lymphocytes/well in RPMI-1640 supplemented with 20% FCS, 2 mM glutamine, 1 mM sodium pyruvate, 5% NCTC-109 (GIBCO, Grand Island, NY), 10 μg/ml gentamycin, $10^{-4}$M hypoxanthine, $4\times10^{-7}$M aminopterin, and $1.6\times10^{-5}$M thymidine. Allogeneic irradiated (2000 R) peripheral blood lymphocytes were added at $1.5\times10^4$/well as feeder cells. Hybrids appeared in 2-3 weeks and were screened for anti-bombesin antibodies by ELISA.

II. Results

Immunofluorescent studies on the two cell populations separated on nylon wool showed that the nonadherent fraction was enriched in T lymphocytes (77% in nonadherent fraction vs. 37% in original population) whereas the adherent fraction was enriched in B lymphocytes (83% in adherent fraction vs. 64% in original population).

The two populations were mixed in equal numbers which resulted in a second population having a T-helper cell to B-cell ratio of about 0.63, and a T-suppressor cell content about equal to that of the original population. This second population was cultured with 20% LCS, 10% human AB serum, 7.5 μg/ml LPS, and soluble BTT. Because the concentration of antigen giving optimal stimulation varied among donors, 3 to 4 doses of BTT ranging from 0.6 ng/ml-6 μg/ml were tested in each experiment. After 6 days of culture, the sensitized cells were fused with NS-1 cells and the hybrids assayed for reactivity with BTT, BTG, TT or TG 3-4 weeks after fusion. A hybrid (BM-1) was selected that produced antibody which bound to BTT and BTG but not TT nor TG. This reactivity pattern strongly suggested the presence of an antibody against bombesin. The use of isotype-specific HRP-conjugated antibodies in the ELISA showed that the specific antibody was IgM. This hybrid was cloned by limiting dilution and its specificity confirmed by titrations in ELISA.

The binding of antibody BM-1 to BTT and BTG, but not TT or TG, strongly suggested that it was an anti-bombesin. However, to further study the specificity of putative anti-bombesin antibodies, competitive inhibition was performed using a dilution of antibody which had been found previously to yield half-maximal binding to BTT. Binding of the BM-1 antibody to BTT was inhibited by precincubation of the hybrid supernatant fluids with bombesin conjugated to TT or TG via ECDI. In contrast, unconjugated TT or TG was not inhibitory. This reactivity pattern confirms that observed in the initial ELISA. To rule out the possibility that the antibody is recognizing a determination on the coupling agent, ECDI, unconjugated [Lys$^3$]-bombesin and BTG prepared by conjugation via glutaraldehyde were included as inhibitors. Both reagents were inhibitory indicating that BM-1 was producing a genuine anti-bombesin antibody.

I claim:

1. A process for the in vitro immunization of an immuno-competent human splenocyte against an immunogen comprising:
   (a) obtaining a first human splenocyte population;
   (b) fractionating the first population by contacting with nylon wool so that a first fraction is enriched with T-cells and a second fraction is enriched with B-cells, wherein said T-cells have subpopulations of T-helper cells and T-suppressor cells;
   (c) mixing together approximately equal numbers of cells from the first and second fractions to form a second population such that the second population has a T-helper cell to B-cell ratio of at least 0.4 and such that the percentage of T-suppressor cells is essentially unchanged from the first population; and
   (d) culturing the second population in a medium containing human serum, an immunogen, and a lymphokine or lymphokines which induce proliferation and differentiation of T and B cells wherein the human serum, the immunogen and the lymphokine or lymphokines are added at initiation of culture.

2. The process of claim 1 wherein step (b) comprises contacting the first B-cell enriched population with nylon wool whereby the second fraction is adsorbed to the nylon wool and the first fraction does not adsorb to nylon wool, the second fraction being subsequently desorbed for use in step (c).

3. The process of claim 1 or 2 wherein "the medium" of step (d) further contains a "monocyte activator".

4. The process of claim 1 or 2 wherein the human serum is "allogeneic".

5. The process of claim 3 wherein the human serum is allogeneic.

6. The process of claim 1 or 2 wherein the immunogen is selected from the group consisting of bacterial antigens, viral antigens, toxins, blood group antigens, lymphoid cell antigens, myosin and tumor antigens.

7. The process of claim 1 or 2 wherein the immunogen is a tumor cell secreted product.

8. The process of claim 6 wherein "the medium" of step (d) further contains a "monocyte activator".

9. The process of claim 6 wherein the human serum is allogeneic.

* * * * *